(12) United States Patent
Liu et al.

(10) Patent No.: US 9,984,772 B2
(45) Date of Patent: May 29, 2018

(54) IMAGE ANALYTICS QUESTION ANSWERING

(71) Applicant: Siemens Healthcare GmbH, Erlangen (DE)

(72) Inventors: Wen Liu, Santa Clara, CA (US); Ashutosh Modi, Saarbruecken (DE); Bogdan Georgescu, Plainsboro, NJ (US); Francisco Pereira, Jersey City, NJ (US)

(73) Assignee: Siemens Healthcare GmbH, Erlangen (DE)

( * ) Notice: Subject to any disclaimer, the term of this patent is extended or adjusted under 35 U.S.C. 154(b) by 0 days. days.

(21) Appl. No.: 15/455,591

(22) Filed: Mar. 10, 2017

(65) Prior Publication Data
US 2017/0293725 A1 Oct. 12, 2017

Related U.S. Application Data

(60) Provisional application No. 62/319,572, filed on Apr. 7, 2016.

(51) Int. Cl.
*G06F 17/27* (2006.01)
*G06F 17/30* (2006.01)
(Continued)

(52) U.S. Cl.
CPC ........... *G16H 50/20* (2018.01); *G06F 17/271* (2013.01); *G06F 17/279* (2013.01);
(Continued)

(58) Field of Classification Search
CPC .... G06F 17/27; G06F 17/2785; G06F 17/279; G06F 17/30401; G06F 17/30427; G06F 17/3043
See application file for complete search history.

(56) References Cited

U.S. PATENT DOCUMENTS 7,492,949 B1 * 2/2009 Jamieson .............. G06F 17/248
382/217
8,112,269 B2 * 2/2012 Cao .................... G06F 17/30654
704/10
(Continued)

OTHER PUBLICATIONS

Extended European Search Report dated Aug. 31, 2017 in corresponding EP application No. 17163780.4.
(Continued)

*Primary Examiner* — Eric Yen

(57) ABSTRACT

A computer-implemented method for predicting answers to questions concerning medical image analytics reports includes splitting a medical image analytics report into a plurality of sentences and generating a plurality of sentence embedding vectors by applying a natural language processing framework to the plurality of sentences. A question related to subject matter included in the medical image analytics report is received and a question embedding vector is generated by applying the natural language processing framework to the question. A subset of the sentence embedding vectors most similar to the question embedding vector is identified by applying a similarity matching process to the sentence embedding vectors and the question embedding vector. A trained recurrent neural network (RNN) is used to determine a predicted answer to the question based on the subset of the sentence embedding vectors.

20 Claims, 4 Drawing Sheets

(51) Int. Cl.
G06F 19/00 (2018.01)
G06N 3/08 (2006.01)
G06N 3/04 (2006.01)

(52) U.S. Cl.
CPC ...... *G06F 17/2785* (2013.01); *G06F 17/3043* (2013.01); *G06F 19/345* (2013.01); *G06N 3/0445* (2013.01); *G06N 3/08* (2013.01)

(56) References Cited

U.S. PATENT DOCUMENTS

| | | | | |
|---|---|---|---|---|
| 2002/0065845 | A1* | 5/2002 | Naito | G06F 17/30634 715/248 |
| 2004/0006567 | A1* | 1/2004 | Kurtz | G06F 17/30722 |
| 2009/0089058 | A1* | 4/2009 | Bellegarda | G06F 17/277 704/251 |
| 2013/0021346 | A1* | 1/2013 | Terman | G09B 5/08 345/467 |
| 2014/0214402 | A1* | 7/2014 | Diao | G06F 17/2745 704/9 |
| 2014/0236578 | A1* | 8/2014 | Malon | G06F 17/28 704/9 |
| 2016/0358094 | A1* | 12/2016 | Fan | G06F 17/3053 |
| 2017/0212872 | A1* | 7/2017 | Albert | G06F 17/2211 |

OTHER PUBLICATIONS

Wikipedia "CUDA", Wikipedia, the free encyclopedia, pp. 1-14, XP055401182, Retrieved from the Internet: URL: https:jjen.wikipedia.orgjwiindex.php?title=CUDA&oldid=713790163 / May 4, 2016.

Jeremy Appleyard et al: "Optimizing Performance of Recurrent Neural Networks on GPUs", arxiv.org, Cornell University Library, 201 Olin Library Cornell University Ithaca, NY, 14853, XP080693971, / Jul. 4, 2016.

Felix Weninger et al: "Introducing CURRENNT", Journal of Machine Learning Research, MIT Press, Cambridge, MA, US, vol. 16, No. I, 2015, pp. 547-551, XP058069848, ISSN: 1532-4435.

Fernando Llopis et al: "Passage selection to improve Question Answering", Multilingual Summarization and Question Answering, Association for Computational; Linguistics, N. Eight Street, Stroudsburg, PA, 18360 07960-1961 USA, pp. 1-6, XP058144577; DOI: 10.3115/ 1118845.1118851 / Aug. 31, 2002.

L. Schwartz. D. M. Panicek, A. R. Berk, Y. Li, H. Hricak. Improving Communication of Diagnostic Radiology Findings through Structured Reporting, 2011 JRSNA.

D. B. Larson, A. J. Towbin, R. M. Pryor, L. F. Donnelly. Improving Consistency in Radiology Reporting through the use of Department-wide Standardized Structured Reporting. 2013 JRSNA.

O. R. Brook, A. Brook, C. M. Vollmer, T. S. Kent, N. Sanchez, I. Pedrosa. Structured Reporting of Multiphasic CT for Pancreatic Cancer: Potential Effect on Staging and Surgical Planning. 2014 JRSNA.

Dan Klein and Christopher D. Manning. 2003 Accurate Unlexicalized Parsing. Proceedings of the 41st Meeting of the Association for Computational Linguistics, pp. 423-430.

Hochreiter, S., & Schmidhuber, J. (1997). Long short-term memory. Neural computation, 9(8), 1735-1780.

S. Varges, H. Bieler, M. Stede, L. C. Faulstich, K. Irsig, M. Atalla. SemScribe: Natural Language Generation for Medical Reports. 2012 ICLR.

Pathak, Sayan D., et al. "Linking DICOM pixel data with radiology reports using automatic semantic annotation." SPIE Medical Imaging. International Society for Optics and Photonics, 2012.

H. Shin, L. Lu, L. Kim, A. Seff, J. Yao, R. M. Summers Interleaved Text/Image Deep Mining on a Large-Scale Radiology Database for Automated Image Interpretation. 2015 JMachineLeaming Research.

J. Hunter, Y. Freer, A. Gatt, E. Reiter, S. Sripada, C. Sykes, D. Westwater. BT-Nurse: computer generation of natural language shift summaries from complex heterogeneous medical data. 2011 JAMIA.

Stabuskaw Antol, Aishwarya Agrawal, Jiasen Lu, Margaret Mitchell, Dhruv Batra, C. Lawrence Zitnick, Devi Parikh. VQA: Visual Question Answering, arXiv:1505.00468v5 [cs.CL] Mar. 7, 2016.

Tomas Mikolov, Kai Chen, Greg Corrado, and Jeffrey Dean. Efficient Estimation of Word Representations in Vector Space. In Proceedings of Workshop at ICLR, 2013.

Savova, G. K., Masanz, J. J., Ogren, P. V., Zheng, J., Sohn, S., Kipper-Schuler, K. C., & Chute, C. G. (2010). Mayo clinical Text Analysis and Knowledge Extraction System (cTAKES): architecture, component evaluation and applications. Journal of the American Medical Informatics Association, 17(5), 507-513.

Yoshua Bengio, Réjean Ducharme, Pascal Vincent, Christian Jauvin. A Neural Probabilistic Language Model. Journal of Machine Learning Research 3 (2003) 1137-1155.

www.Radreport.org; 2017.

American College of Radiology. Liver Imaging Reporting and Data System version 2014; http://www.acr.org/Quality-Safety/Resources/LIRADS.

Natural Language Toolkit: http://www.nitk.org/ ; 2017.

\* cited by examiner

Radiology Report

300 —

The liver presents a newly occurred hypodense lesion in segment 2 (2.8x2.1 cm, image 54). The liver shows a hypodense, clearly limited lesion of constant size in segment 6, with up to 0.6 cm (images 62, 63, 64), which is most likely cystic. The intra- and extrahepatic bile ducts are normal wide. The gallbladder is filled. The adrenals present new nodular lesions in the left adrenal measuring 2.5x1.2 cm at the medial crus (image 61) and 2.7x1.8 cm at the lateral crus (image 65), and on the right measuring 1.5x0.7 cm at the medial crus (image 61). Both kidneys are in orthotopic position. The kidneys show simultaneous contrast enhancement. The kidneys presents new hypodense lesion. The right kidney presents a lesion at the middle level with 1.8x1.2 cm (image 81). The left kidney presents a lesion and at the middle with 1.9x1.5 cm (image 73). There are no urinary constructions.

Question

Where is the largest hypodense lesion in the liver?

Pipeline for answering the question based on the report

Possible Answers

The liver presents a newly occurred hypodense lesion in segment 2 (2.8x2.1 cm, image 54).

The liver shows a hypodense, clearly limited lesion of constant size in segment 6, with up to 0.6 cm (images 62, 63, 64), which is most likely cystic.

The kidneys presents new hypodense lesion.

*Fig. 3* ific domain and ontology to derive text descriptions for report,

IMAGE ANALYTICS QUESTION ANSWERING

CROSS-REFERENCE TO RELATED APPLICATIONS

This application claims the benefit of U.S. Provisional Application Ser. No. 62/319,572 filed Apr. 7, 2016, which is incorporated herein by reference in its entirety.

TECHNOLOGY FIELD

The present invention relates generally to methods, systems, and apparatuses for automatically understanding results from image analytics through a question answering system. Using the disclosed methods, systems, and apparatuses may be applied to the processing for information gathered from a variety of imaging modalities including, without limitation, Computed Tomography (CT), Magnetic Resonance (MR), Positron Emission Tomography (PET), and Ultrasound (US) technologies.

BACKGROUND

Traditionally, medical image radiology reports are created by transcribing a recording of interpretations of the image data by a radiologist. This results in an unstructured collection of findings subject to the experience and organization of individual radiologists, which varies in syntax and semantics. In contrast, recent studies have shown the advantages of consistent communication and superior evaluation from structured radiology reports. As such there are several ongoing radiology initiatives to standardize templates and lexicography.

Research in natural language processing of medical data have developed models to represent the linguistics and language of reporting by creating a comprehensive interpretation of diagnostic semantics. Recently, work from the National Institute of Heath presented the first study performing a large-scale image/text analysis on a hospital picture archiving and communication system database. While previous studies and proprietary efforts mainly focus on specific domain and ontology to derive text descriptions for report, there is a need for a generic architecture which can accommodate different forms of analytical data as well as being adaptable to multiple clinical domains.

SUMMARY

Embodiments of the present invention address and overcome one or more of the above shortcomings and drawbacks, by providing methods, systems, and apparatuses related to automatically understanding the results presented in image analytics reports through a question answering system. These techniques described herein can be applied towards generating natural language findings to fill out a structured radiology report. The use of standardized report templates and fields will streamline comparison to longitudinal data and similar cases from the past reports, which allows this system to quickly process and interpret the current patient data in the context of historical big data.

According to some embodiments, a computer-implemented method for predicting answers to questions concerning medical image analytics reports includes splitting a medical image analytics report into the sentences and generating the sentence embedding vectors by applying a natural language processing framework to the sentences. A question related to subject matter included in the medical image analytics report is received and a question embedding vector is generated by applying the natural language processing framework to the question. A subset of the sentence embedding vectors most similar to the question embedding vector is identified by applying a similarity matching process to the sentence embedding vectors and the question embedding vector. A trained recurrent neural network (RNN) is used to determine a predicted answer to the question based on the subset of the sentence embedding vectors. In some embodiments, the trained RNN is a long short-term memory (LSTM) RNN and the predicted answer is determined by dividing the subset of the sentence embedding vectors into a first sequence of words and dividing the subset of the question embedding vector into a second sequence of words. The first sequence of words and the second sequence of words are passed through the LSTM cells sequentially to yield the outputs corresponding to different states. The outputs are combined using linear operations into a single input vector and a softmax function is applied to the single input vector to generate the predicted answer.

Various refinements, enhancements, and other modifications can be made to the aforementioned method in different embodiments of the present invention. For example, in one embodiment, each sentence embedding vector is created by first generating an embedding for each word in a particular sentence using the natural language processing framework. Then, the embedding of each word in the particular sentence is averaged to yield the sentence embedding vector. The natural language processing framework may identify the target medical syntax, for example, by matching the sentences to one or more ontology references such as a Unified Medical Language System (UMLS) dataset. The target medical syntax may include a description of one or more diseases and/or a description of one or more anatomical entities. In some embodiments, the natural language processing framework is trained with one or more medical knowledge datasets such as radiology guidelines from the American College of Radiology.

In some embodiments of the aforementioned method, the similarity matching process includes calculating a cosine product between each sentence embedding vector and the question embedding vector to yield a similarity score for each sentence embedding vector. The sentence embedding vectors are ranked according to similarity score and a predetermined number of the highest ranking sentence embedding vectors are selected as the subset of the sentence embedding vectors.

According to another aspect of the present invention, a computer-implemented method for predicting answers to questions concerning medical image analytics reports includes generating sentence embedding vectors by applying a natural language processing framework to sentences in a medical image analytics report. A question related to subject matter included in the medical image analytics report is received and a question embedding vector is generated by applying the natural language processing framework to the question. The subset of the sentence embedding vectors most similar to the question embedding vector is identified and divided into a first sequence of words. The subset of the question embedding vector is divided into a second sequence of words. The first sequence of words and the second sequence of words are passed through a plurality of LSTM cells sequentially to yield a plurality of outputs corresponding to different states. The outputs are combined into a single input vector and a softmax function is applied to the single input vector to generate a predicted answer.

According to other embodiments, a system for predicting answers to questions concerning medical image analytics reports includes a host computer comprising one or more processors and a device computer comprising a graphics processing unit (GPU). The processors of the host computer is configured to generate a plurality of sentence embedding vectors by applying a natural language processing framework to the plurality of sentences included in a medical image analytics report. The processors are further configured to receive a question related to subject matter included in the medical image analytics report and generate a question embedding vector by applying the natural language processing framework to the question. Additionally, the processor identifies a subset of the sentence embedding vectors most similar to the question embedding vector by applying a similarity matching process to the sentence embedding vectors and the question embedding vector. The device computer uses a LSTM-based RNN to determine a predicted answer to the question based on the subset of the sentence embedding vectors. Each element included in the subset of the sentence embedding vectors is processed by a LSTM cell in parallel using processing resources of the GPU.

Additional features and advantages of the invention will be made apparent from the following detailed description of illustrative embodiments that proceeds with reference to the accompanying drawings.

BRIEF DESCRIPTION OF THE DRAWINGS

The foregoing and other aspects of the present invention are best understood from the following detailed description when read in connection with the accompanying drawings. For the purpose of illustrating the invention, there are shown in the drawings embodiments that are presently preferred, it being understood, however, that the invention is not limited to the specific instrumentalities disclosed. Included in the drawings are the following Figures:

FIG. 3 shows an example application of the pipeline described above with reference to FIG. 1.

DETAILED DESCRIPTION OF ILLUSTRATIVE EMBODIMENTS

The following disclosure describes the present invention according to several embodiments directed at methods, systems, and apparatuses related to techniques for understanding image analytics results through a question answering system. More specifically, the techniques described herein are capable of demonstrating an understanding of results from image analytics through a question answering system. Given a set of results from image analytics and a natural language question about the data, the system is capable of providing an accurate natural language answer. Answering such questions require a detailed understanding of the image, language and reasoning within the appropriate image context. This includes, for example, radiologic readings of medical image data, where quantitative and qualitative measurements from image parsing can be collected as results from image analytics and answers to questions regarding the image data to fill out a radiology report. In the context of radiology reporting, the main challenge of such a system is to overcome data sparsity from unbalanced data representation and inconsistent quality of annotations. To address these challenges the techniques described herein leverage natural language processing parsing to select medical syntax and learn a language embedding from large medical text corpus. The question answering system described herein is flexible and adaptable to different (spoken) languages for the generated reports, templates and clinical report concepts.

Figure 1:
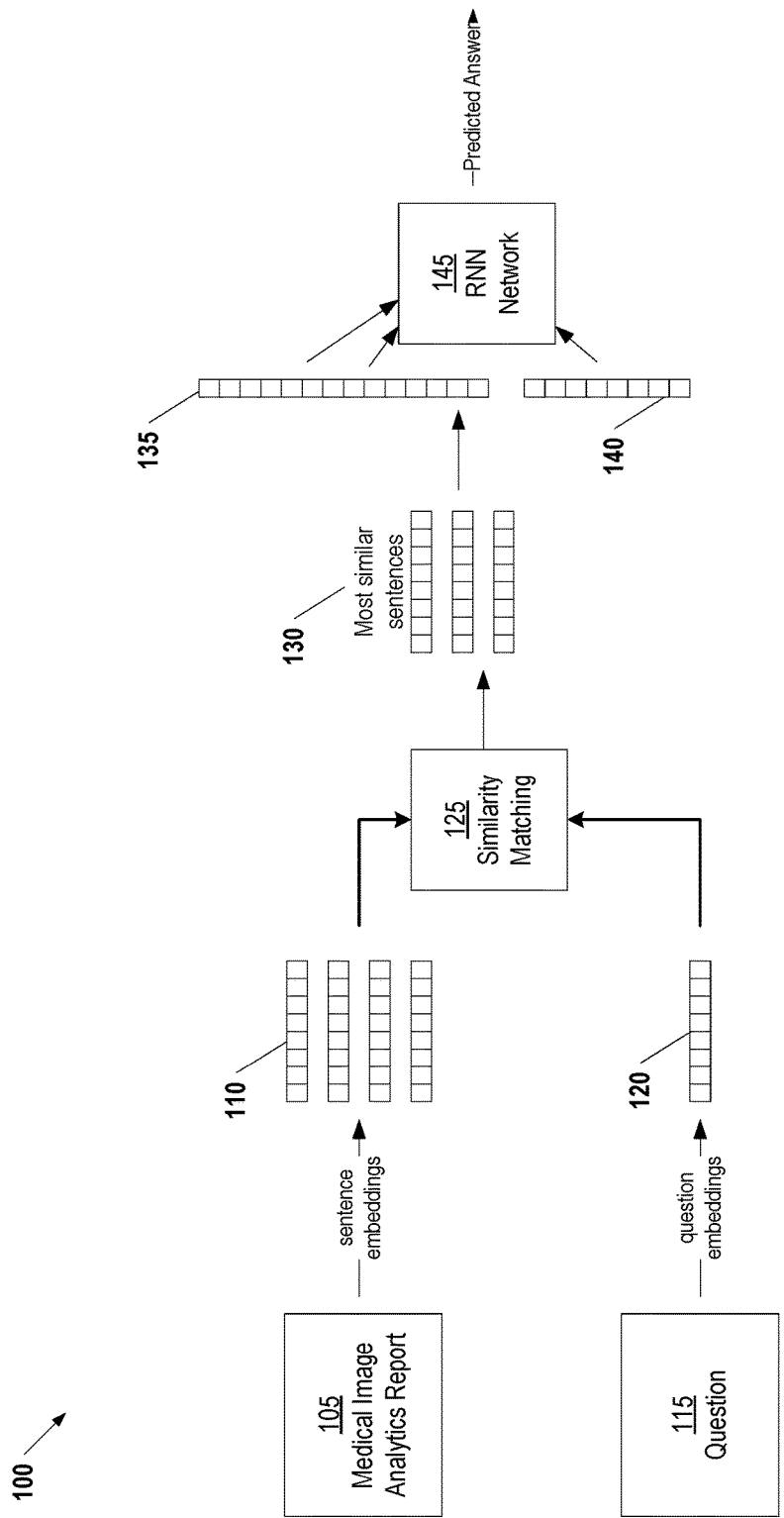
FIG. 1 illustrates a pipeline for answering a question based on a report, according to some embodiments.

FIG. 1 illustrates a pipeline 100 for answering a question based on a report, according to some embodiments. In conventional systems, reading and reporting from medical images is a manual unstructured task subject to human interpretation of not only the current data but also in reference to historical information. To improve this process, pipeline 100 uses a trained image analytics question answering system to generate natural language findings for structured radiology reports. The input data comprises results from the analysis of diagnostic image data, their radiology reports and related non-image patient meta-data. These results provide dense anatomical or functional qualitative and quantitative measurements. Optional requirements include a large medical text corpus in the appropriate medical domain.

At the initial stage of the pipeline, a medical image analytics report 105 (e.g., a radiology report) is split into sentences using techniques generally known in the art. Next, a plurality of sentence embedding vectors 110 are generated by applying a natural language processing framework to the sentences from the medical image analytics report 105. The term "embedding," as used herein refers to words or phrases from the vocabulary are mapped to vectors of real numbers. An embedding simultaneously provides a distributed representation for each word along with the probability function for word sequences. Thus, the sentence embedding vectors 110 captures the semantics of the sentence. In some embodiments, the sentence embedding vectors 110 are calculated by taking an average of the embedding of each of the word in the corresponding sentence. The embedding for each of the word may be obtained by training a model (e.g., word2vec) over a large bio-medical corpus (e.g., Pub Med Central).

Various natural language processing frameworks known in the art can be used to create the sentence embedding 110 including, without limitation, Apache cTAKES, Stanford Parser, and NLTK. The framework used in generating the embedding is specifically trained to the clinical domain related to the subject matter of medical image analytics report 105. The purpose of this training is twofold. First, target medical syntax, such as known anatomical entities and diseases, as indicated by patient medical history and image acquisition objectives will be located and prioritized by matching to standard ontology references (e.g., Unified Medical Language System). Second, semantic parsing will help address ambiguities or mistakes created from lower-quality annotations. Emphasizing known key words, and their role in the semantics of the training data, allows us to address the challenge of inconsistent quality of annotations.

In some embodiments, a learned embedding of established medical knowledge bases (e.g., radiology guidelines from the American College of Radiology) is integrated into training. Leveraging medical text corpus informs the model of the semantic relationships of neighboring words and phrases used in radiology reports. Training such large models (with millions of parameters) within a reasonable time is itself a significant challenge. However, as discussed below with respect to FIG. 4, processing time can be minimized through the use of parallel computing platforms such as NVIDIA CUDA™.

Continuing with reference to FIG. 1, question 115 relates to the subject matter of the medical image analytics report 105. This question 115 is used to generate a question embedding vector 120 by applying the natural language processing framework to the question 115. The techniques and motivation for using the natural language processing framework for question processing are similar to those discussed above with respect to the medical image analytics report 105. The question 115 can be of any form including, but not limited to binary, multiple choice, or opened ended. In general, the question may be received and interpreted using any technique known in the art. Thus, in some embodiments, a clinician may type the question 115 into a graphical user interface (GUI) associated with medical image analytics software (or similar software). Alternatively, the question 115 may be extracted from a larger text (e.g., an email). Additionally, in embodiments where the question 115 is spoken by the clinician, the question may be interpreted and translated into text form using speech-to-text techniques generally known in the art.

Answering a question would require understanding the text in the medical analytics report and narrowing down attention on specific sentences which potentially contain the answer. The pipeline implements this local attention focusing mechanism by calculating the similarity between the sentences in the report and the question. More specifically, as shown in FIG. 1, a similarity matching process 125 is applied to the sentence embedding vectors 110 and the question embedding vector 120 to generate a similarity score for each of the sentence embedding vectors 110. In some embodiments, the similarity score is generated by calculating the cosine product between the two embedding vectors. Based on the similarity score, the sentences are then ranked by this similarity score and we select the top k (e.g., 5) sentences. If the similarity score is representative of good semantic match then these top k sentences should contain the information required for answering.

At the final stage of the pipeline, words 135 from the most similar sentences and words 140 from the question are used as input to a trained recurrent neural network (RNN) to determine a predicted answer to the question. Answers can be full sentences, or sentence fragments that are either generated or matched. The overall pipeline is amenable to automatic evaluation, since many open-ended answers contain only a few words or a closed set of answers that can be provided in a multiple choice format. In some embodiments, the answer explains a specific clinical finding in the report by indicating the image features used to derive it.

Figure 2:
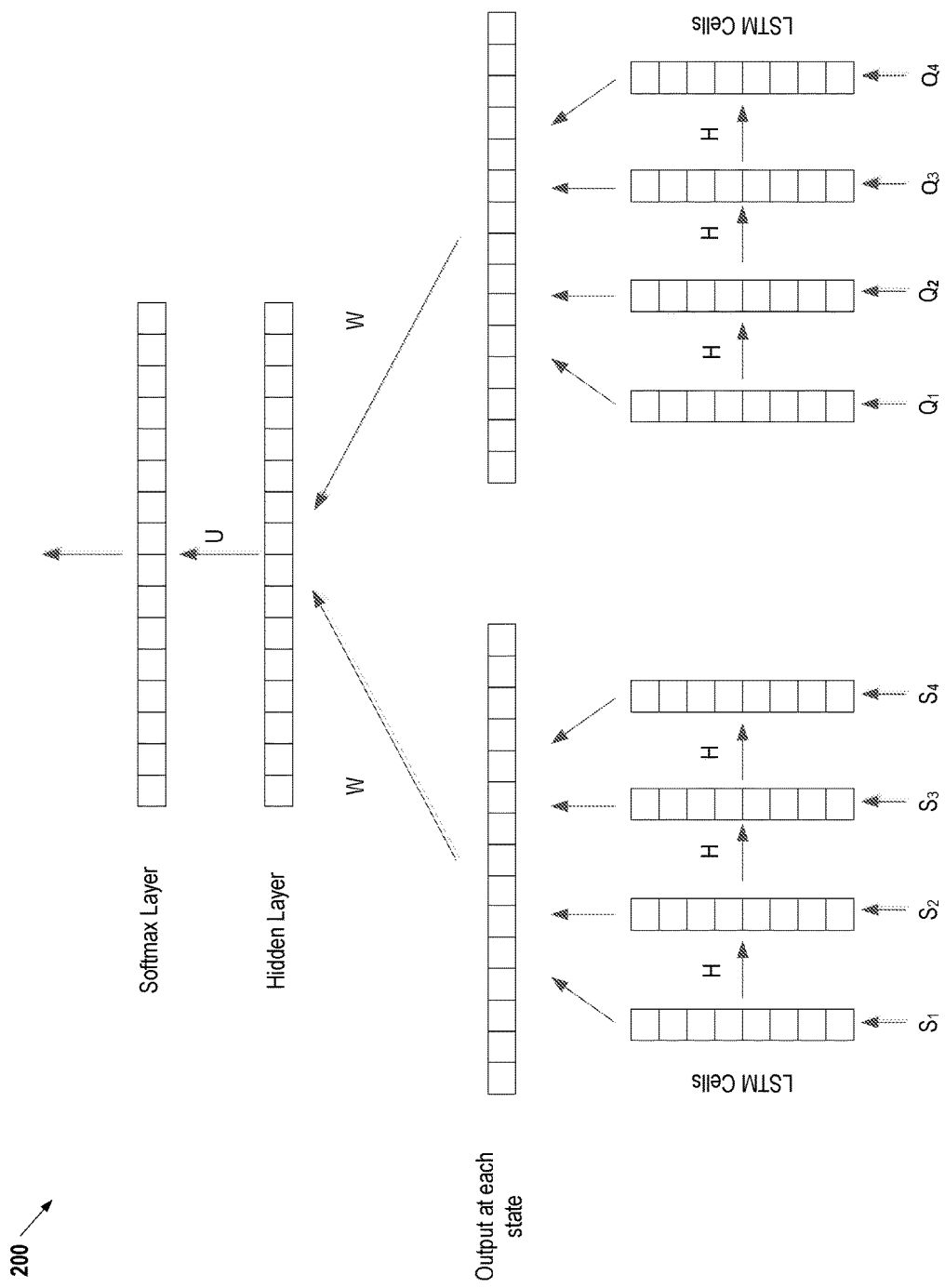
FIG. 2 illustrates an example where a LSTM (Long Short Term Memory) based RNN is applied for answering a question, according to some embodiments.

The RNN used in the pipeline can generally be any artificial neural network where connections between units form a directed cycle. FIG. 2 illustrates an example where a LSTM (Long Short Term Memory) based RNN is applied for answering the question. Input to the network is sequence of words ($S_1$, S2 etc.) from the sentence and the question ($Q_1$, Q2 etc.) These are passed through the LSTM cells sequentially. Output at each state is passed into another hidden layer and all these are combined via linear operations to be passed into a softmax function, to predict the answer.

FIG. 3 shows an example application of the pipeline 100 described above with reference to FIG. 1. Here, the medical image analytics report is a radiology report and a question has been posed "where is the largest hypodense lesion in the liver." In this case, rather than provide a single answer following application of the RNN in the pipeline, three possible answers are suggested. These may be, for example, the top three results according to a probability measure of the RNN. The ability to see several possible answers to the question may be used for testing the pipeline versus ground truth. However, this functionality also has diagnostics benefits because each possible answer includes different relevant information that could be of interest to the clinician that posed the original question.

In some embodiments, the pipeline 100 is a component which can be incorporated into the generation of natural language findings in a workflow for automated radiology reporting and other medical imaging processing. Such a workflow and related systems are described in U.S. patent application Ser. No. 15/158,375 filed May 18, 2016, entitled "Automatic Generation of Radiology Reports from Images and Automatic Rule Out of Images without Findings," the entirety of which is incorporated herein by reference.

Figure 4:
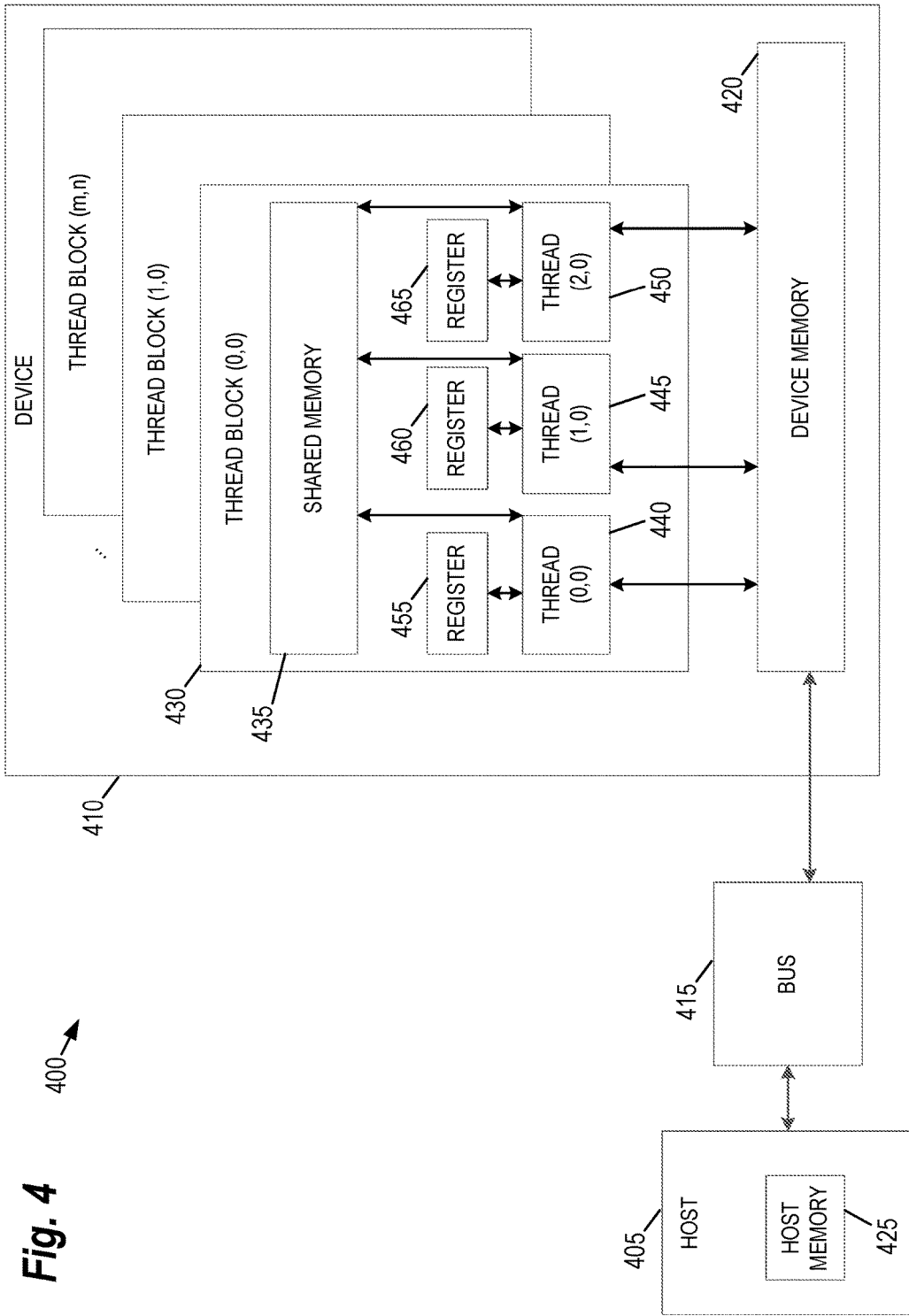
FIG. 4 provides an example of a parallel processing memory architecture 400 that may be utilized to implement the pipeline shown FIG. 1, according to some embodiments of the present invention.

FIG. 4 provides an example of a parallel processing memory architecture 400 that may be utilized to implement the pipeline 100 shown FIG. 1, according to some embodiments of the present invention. This architecture 400 may be used in embodiments of the present invention where NVIDIA CUDA™ (or a similar parallel computing platform) is used. The architecture includes a host computing unit ("host") 405 and a graphics processing unit (GPU) device ("device") 410 connected via a bus 415 (e.g., a PCIe bus). The host 405 includes the central processing unit, or "CPU" (not shown in FIG. 4), and host memory 425 accessible to the CPU. The device 410 includes the graphics processing unit (GPU) and its associated memory 420, referred to herein as device memory. The device memory 420 may include various types of memory, each optimized for different memory usages. For example, in some embodiments, the device memory includes global memory, constant memory, and texture memory.

Parallel portions of a big data platform and/or big simulation platform (see FIG. 4) may be executed on the architecture 400 as "device kernels" or simply "kernels." A kernel comprises parameterized code configured to perform a particular function. The parallel computing platform is configured to execute these kernels in an optimal manner across the architecture 400 based on parameters, settings, and other selections provided by the user. Additionally, in some embodiments, the parallel computing platform may include additional functionality to allow for automatic processing of kernels in an optimal manner with minimal input provided by the user.

The processing required for each kernel is performed by grid of thread blocks (described in greater detail below). Using concurrent kernel execution, streams, and synchronization with lightweight events, the architecture 400 of FIG. 4 (or similar architectures) may be used to parallelize portions of the model based operations performed in training or utilizing the pipeline 100. For example, in some embodiments, training of the natural language format or application of the RNN in the framework may be performed. In other embodiments, the LSTM cells (see FIG. 2) may be used to analyze elements of each embedding vector in parallel.

The device 410 includes one or more thread blocks 430 which represent the computation unit of the device 410. The term thread block refers to a group of threads that can cooperate via shared memory and synchronize their execution to coordinate memory accesses. For example, in FIG. 4, threads 440, 445 and 450 operate in thread block 430 and access shared memory 435. Depending on the parallel computing platform used, thread blocks may be organized in a grid structure. A computation or series of computations may then be mapped onto this grid. For example, in embodiments utilizing CUDA, computations may be mapped on one-, two-, or three-dimensional grids. Each grid contains multiple thread blocks, and each thread block contains multiple threads. For example, in FIG. 4, the thread blocks 430 are organized in a two dimensional grid structure with m+1 rows and n+1 columns. Generally, threads in different thread blocks of the same grid cannot communicate or synchronize with each other. However, thread blocks in the same grid can run on the same multiprocessor within the GPU at the same time. The number of threads in each thread block may be limited by hardware or software constraints.

Continuing with reference to FIG. 4, registers 455, 460, and 465 represent the fast memory available to thread block 430. Each register is only accessible by a single thread. Thus, for example, register 455 may only be accessed by thread 440. Conversely, shared memory is allocated per thread block, so all threads in the block have access to the same shared memory. Thus, shared memory 435 is designed to be accessed, in parallel, by each thread 440, 445, and 450 in thread block 430. Threads can access data in shared memory 435 loaded from device memory 420 by other threads within the same thread block (e.g., thread block 430). The device memory 420 is accessed by all blocks of the grid and may be implemented using, for example, Dynamic Random-Access Memory (DRAM).

Each thread can have one or more levels of memory access. For example, in the architecture 400 of FIG. 4, each thread may have three levels of memory access. First, each thread 440, 445, 450, can read and write to its corresponding registers 455, 460, and 465. Registers provide the fastest memory access to threads because there are no synchronization issues and the register is generally located close to a multiprocessor executing the thread. Second, each thread 440, 445, 450 in thread block 430, may read and write data to the shared memory 435 corresponding to that block 430. Generally, the time required for a thread to access shared memory exceeds that of register access due to the need to synchronize access among all the threads in the thread block. However, like the registers in the thread block, the shared memory is typically located close to the multiprocessor executing the threads. The third level of memory access allows all threads on the device 410 to read and/or write to the device memory. Device memory requires the longest time to access because access must be synchronized across the thread blocks operating on the device. Thus, in some embodiments, the processing of each sentence included in a report (or the processing of the sentence's corresponding embedding) is coded such that it primarily utilizes registers and shared memory and only utilizes device memory as necessary to move data in and out of a thread block.

The embodiments of the present disclosure may be implemented with any combination of hardware and software. For example, aside from parallel processing architecture presented in FIG. 4, standard computing platforms (e.g., servers, desktop computer, etc.) may be specially configured to perform the techniques discussed herein. In addition, the embodiments of the present disclosure may be included in an article of manufacture (e.g., one or more computer program products) having, for example, computer-readable, non-transitory media. The media may have embodied therein computer readable program code for providing and facilitating the mechanisms of the embodiments of the present disclosure. The article of manufacture can be included as part of a computer system or sold separately.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

An executable application, as used herein, comprises code or machine readable instructions for conditioning the processor to implement predetermined functions, such as those of an operating system, a context data acquisition system or other information processing system, for example, in response to user command or input. An executable procedure is a segment of code or machine readable instruction, sub-routine, or other distinct section of code or portion of an executable application for performing one or more particular processes. These processes may include receiving input data and/or parameters, performing operations on received input data and/or performing functions in response to received input parameters, and providing resulting output data and/or parameters.

A graphical user interface (GUI), as used herein, comprises one or more display images, generated by a display processor and enabling user interaction with a processor or other device and associated data acquisition and processing functions. The GUI also includes an executable procedure or executable application. The executable procedure or executable application conditions the display processor to generate signals representing the GUI display images. These signals are supplied to a display device which displays the image for viewing by the user. The processor, under control of an executable procedure or executable application, manipulates the GUI display images in response to signals received from the input devices. In this way, the user may interact with the display image using the input devices, enabling user interaction with the processor or other device.

The functions and process steps herein may be performed automatically or wholly or partially in response to user command. An activity (including a step) performed automatically is performed in response to one or more executable instructions or device operation without user direct initiation of the activity.

The system and processes of the figures are not exclusive. Other systems, processes and menus may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. As described herein, the various systems, subsystems, agents, managers and processes can be implemented using hardware components, software components, and/or combinations thereof. No claim element herein is to be construed under the provisions of 35 U.S.C. 112, sixth paragraph, unless the element is expressly recited using the phrase "means for."

We claim:
1. A computer-implemented method for predicting answers to questions concerning medical image analytics reports, the method comprising:
   splitting a medical image analytics report into a plurality of sentences;

generating a plurality of sentence embedding vectors by applying a natural language processing framework to the plurality of sentences;

receiving a question related to subject matter included in the medical image analytics report;

generating a question embedding vector by applying the natural language processing framework to the question;

identifying a subset of the sentence embedding vectors most similar to the question embedding vector by applying a similarity matching process to the sentence embedding vectors and the question embedding vector; and using a trained recurrent neural network (RNN) to determine a predicted answer to the question based on the subset of the sentence embedding vectors.

2. The method of claim 1, wherein each respective sentence embedding vector is generated by:

generating an embedding for each word in a particular sentence using the natural language processing framework; and averaging the embedding of each word in the particular sentence to yield the respective sentence embedding vector.

3. The method of claim 1, wherein the natural language processing framework identifies target medical syntax by matching the plurality of sentences to one or more ontology references.

4. The method of claim 3, wherein the target medical syntax comprises a description of one or more diseases.

5. The method of claim 3, wherein the target medical syntax comprises a description of one or more anatomical entities.

6. The method of claim 3, wherein the one or more ontology references include a Unified Medical Language System (UMLS) dataset.

7. The method of claim 1, further comprising:

training the natural language processing framework with one or more medical knowledge datasets.

8. The method of claim 7, wherein the one or more medical knowledge datasets include radiology guidelines from the American College of Radiology.

9. The method of claim 1, wherein the similarity matching process comprises:

calculating a cosine product between each sentence embedding vector and the question embedding vector to yield a similarity score for each sentence embedding vector;

ranking the sentence embedding vectors according to similarity score; and selecting a predetermined number of highest ranking sentence embedding vectors as the subset of the sentence embedding vectors.

10. The method of claim 1, wherein the trained RNN is a long short-term memory (LSTM) RNN and the predicted answer is determined by:

dividing the subset of the sentence embedding vectors into a first sequence of words;

dividing the question embedding vector into a second sequence of words;

passing the first sequence of words and the second sequence of words through a plurality of LSTM cells sequentially to yield a plurality of outputs corresponding to different states;

combining the plurality of outputs using linear operations into a single input vector; and applying a softmax function to the single input vector to generate the predicted answer.

11. A computer-implemented method for predicting answers to questions concerning medical image analytics reports, the method comprising:

generating a plurality of sentence embedding vectors by applying a natural language processing framework to sentences in a medical image analytics report;

receiving a question related to subject matter included in the medical image analytics report;

generating a question embedding vector by applying the natural language processing framework to the question;

identifying a subset of the sentence embedding vectors most similar to the question embedding vector;

dividing the subset of the sentence embedding vectors into a first sequence of words;

dividing the question embedding vector into a second sequence of words;

passing the first sequence of words and the second sequence of words through a plurality of long short-term memory (LSTM) cells sequentially to yield a plurality of outputs corresponding to different states;

combining the plurality of outputs into a single input vector; and applying a softmax function to the single input vector to generate a predicted answer.

12. The method of claim 11, wherein the subset of the sentence embedding vectors most similar to the question embedding vector are identified by applying a similarity matching process to the sentence embedding vectors and the question embedding vector.

13. The method of claim 11, wherein each respective sentence embedding vector is generated by:

generating an embedding for each word in a particular sentence using the natural language processing framework; and averaging the embedding of each word in the particular sentence to yield the respective sentence embedding vector.

14. The method of claim 11, wherein the natural language processing framework identifies target medical syntax by matching the plurality of sentences to one or more ontology references.

15. The method of claim 14, wherein the target medical syntax comprises a description of one or more diseases.

16. The method of claim 14, wherein the target medical syntax comprises a description of one or more anatomical entities.

17. The method of claim 11, further comprising:

training the natural language processing framework with one or more medical knowledge datasets.

18. The method of claim 17, wherein the one or more medical knowledge datasets include radiology guidelines from the American College of Radiology.

19. The method of claim 12, wherein the similarity matching process comprises:

calculating a cosine product between each sentence embedding vector and the question embedding vector to yield a similarity score for each sentence embedding vector;

ranking the sentence embedding vectors according to similarity score;

selecting a predetermined number of highest ranking sentence embedding vectors as the subset of the sentence embedding vectors.

20. A system for predicting answers to questions concerning medical image analytics reports, the system comprising:

a host computer comprising one or more processors configured to:

generate a plurality of sentence embedding vectors by applying a natural language processing framework to a plurality of sentences included in a medical image analytics report;

receive a question related to subject matter included in the medical image analytics report;

generate a question embedding vector by applying the natural language processing framework to the question;

identify a subset of the sentence embedding vectors most similar to the question embedding vector by applying a similarity matching process to the sentence embedding vectors and the question embedding vector; and a device computer comprising a graphics processing unit (GPU) configured to use a long short-term memory (LSTM)-based recurrent neural network (RNN) to determine a predicted answer to the question based on the subset of the sentence embedding vectors, wherein each element included in the subset of the sentence embedding vectors is processed by a LSTM cell in parallel using processing resources of the GPU.

* * * * *